United States Patent
Goerz et al.

(10) Patent No.: US 12,239,470 B2
(45) Date of Patent: Mar. 4, 2025

(54) STERILISATION CONTAINER FOR RECEIVING STERILE MEDICAL GOODS

(71) Applicant: Aesculap AG, Tuttlingen (DE)

(72) Inventors: Dennis Goerz, Tuttlingen (DE); Bianca Rosin, Tuttlingen (DE); Eva Streit, Bodman-Ludwigshafen (DE); Timo Knittel, Wurmlingen (DE); Stephan Bauer, Emmingen (DE); Corvin Motz, Pfullendorf (DE); Michael Reuter, Leibertingen-Thalheim (DE)

(73) Assignee: Aesculap AG, Tuttlingen (DE)

( * ) Notice: Subject to any disclaimer, the term of this patent is extended or adjusted under 35 U.S.C. 154(b) by 0 days.

(21) Appl. No.: 18/662,122

(22) Filed: May 13, 2024

(65) Prior Publication Data

US 2024/0325105 A1    Oct. 3, 2024

Related U.S. Application Data

(63) Continuation of application No. 17/772,114, filed as application No. PCT/EP2020/080009 on Oct. 26, 2020, now Pat. No. 12,048,569.

(30) Foreign Application Priority Data

Oct. 28, 2019    (DE) ...................... 10 2019 129 061.9

(51) Int. Cl.
*A61B 50/34*    (2016.01)
*A61L 2/26*    (2006.01)
(Continued)

(52) U.S. Cl.
CPC ................ *A61B 50/34* (2016.02); *A61L 2/26* (2013.01); *A61B 2050/005* (2016.02);
(Continued)

(58) Field of Classification Search
CPC .............. A61B 50/34; A61B 2050/005; A61B 2050/0075; A61B 2050/3007;
(Continued)

(56) References Cited

U.S. PATENT DOCUMENTS

| | | |
|---|---|---|
| 4,541,992 A | 9/1985 | Jerge et al. |
| 4,730,729 A | 3/1988 | Monch |

(Continued)

FOREIGN PATENT DOCUMENTS

| | | |
|---|---|---|
| CN | 205418445 U | 8/2016 |
| DE | 7439414 U | 4/1975 |

(Continued)

OTHER PUBLICATIONS

Office Action received in Chinese Application No. 202080074310.1 dated Aug. 21, 2024, with translation, 9 pages.

(Continued)

*Primary Examiner* — Jacob K Ackun
(74) *Attorney, Agent, or Firm* — Christopher A. Rothe; CM Law

(57) ABSTRACT

A sterilization container for receiving cleaned or sterilized medical goods or medical goods to be cleaned or sterilized. The container includes a sterilization container lower part forming a receiving space for the goods and a sterilization container lid that can be detachably mounted on the sterilization container lower part to seal the receiving space. At least one handle element is located on the sterilization container lower part and can be positioned between a carrying position projecting from the sterilization container lid and a locking position that locks the sterilization container lid to the sterilization container lower part. A receiving region is formed in the sterilization container lid for receiving the handle element in the locking position. The receiving region is a trough like handle recess in the form of a (Continued)

Figure 1:
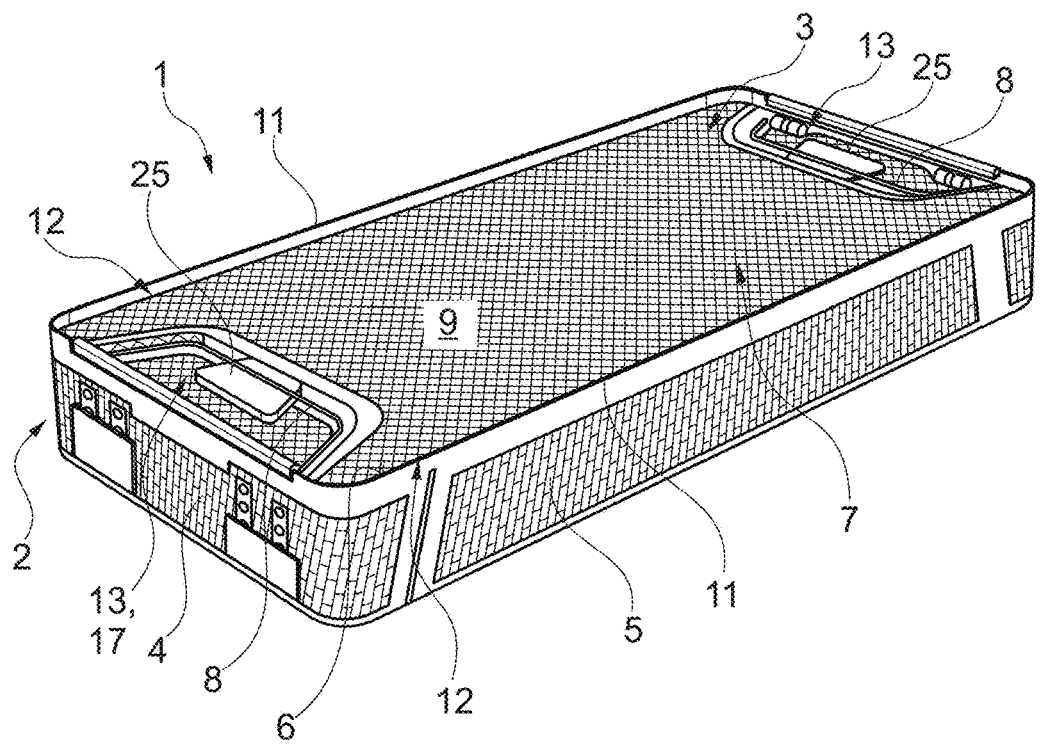

depression projecting into the receiving space with respect to the lid plane for receiving the entire handle element.

13 Claims, 3 Drawing Sheets

(51) Int. Cl.
    *A61B 50/00*     (2016.01)
    *A61B 50/30*     (2016.01)

(52) U.S. Cl.
    CPC .............. *A61B 2050/0075* (2016.02); *A61B 2050/3007* (2016.02); *A61B 2050/3011* (2016.02); *A61L 2202/17* (2013.01); *A61L 2202/182* (2013.01); *A61L 2202/24* (2013.01)

(58) Field of Classification Search
    CPC ............ A61B 2050/3011; A61L 2/26; A61L 2202/17; A61L 2202/182; A61L 2202/24
    USPC ....................................................... 206/370
    See application file for complete search history.

(56) References Cited

U.S. PATENT DOCUMENTS

| | | | |
|---|---|---|---|
| 5,065,885 | A | 11/1991 | Scaroni |
| 5,424,048 | A | 6/1995 | Riley |
| 5,540,901 | A | 7/1996 | Riley |
| 6,012,577 | A | 1/2000 | Lewis et al. |
| 6,116,452 | A * | 9/2000 | Hamel .................. B65D 45/20 220/345.2 |
| 6,152,318 | A | 11/2000 | Walker |
| 6,350,418 | B1 | 2/2002 | Venderpool et al. |
| 8,272,508 | B2 | 9/2012 | Bettenhausen et al. |
| 8,544,648 | B2 | 10/2013 | Cleveland et al. |
| 8,668,111 | B2 | 3/2014 | Orr |
| 8,915,363 | B2 | 12/2014 | Hawkes et al. |
| 11,071,605 | B2 | 7/2021 | Goerz et al. |
| 12,048,569 | B2 * | 7/2024 | Goerz .................. A61B 50/34 |
| 2003/0118491 | A1 | 6/2003 | Frieze et al. |
| 2004/0129595 | A1 | 7/2004 | Dane et al. |
| 2004/0144670 | A1 | 7/2004 | Riley |
| 2005/0158222 | A1 | 7/2005 | Bettenhausen et al. |
| 2006/0144743 | A1 | 7/2006 | McDade |
| 2007/0205123 | A1 | 9/2007 | Bettenhausen et al. |
| 2007/0212277 | A1 | 9/2007 | Riley |
| 2007/0215507 | A1 | 9/2007 | Glenn et al. |
| 2008/0116098 | A1 | 5/2008 | Marooflan et al. |
| 2008/0190932 | A1 | 8/2008 | Orr |
| 2009/0146032 | A1 | 6/2009 | Bettenhausen et al. |
| 2009/0223972 | A1 | 9/2009 | Allen |
| 2011/0155613 | A1 | 6/2011 | Koenig et al. |
| 2012/0195792 | A1 | 8/2012 | Duddy et al. |
| 2013/0105346 | A1 | 5/2013 | Ramkhelawan et al. |
| 2013/0108503 | A1 | 5/2013 | Ramkhelawan et al. |
| 2014/0027330 | A1 | 1/2014 | Lavelle |
| 2014/0077435 | A1 | 3/2014 | Powell |
| 2014/0216966 | A1 | 8/2014 | Ramkhelawan et al. |
| 2014/0339114 | A1 | 11/2014 | Griffin |
| 2016/0151526 | A1 | 6/2016 | Roudebush et al. |
| 2017/0224434 | A1 | 8/2017 | Schwartzbauer et al. |
| 2018/0028703 | A1 | 2/2018 | McLaughlin et al. |
| 2018/0221525 | A1 | 8/2018 | Houde et al. |
| 2019/0201571 | A1 | 7/2019 | Lucier et al. |
| 2021/0259797 | A1 | 8/2021 | Görz et al. |
| 2022/0054216 | A1 | 2/2022 | Goerz et al. |
| 2022/0125543 | A1 | 4/2022 | Birkbeck et al. |
| 2022/0175999 | A1 | 6/2022 | Klemm et al. |
| 2022/0370166 | A1 | 11/2022 | Goerz et al. |

FOREIGN PATENT DOCUMENTS

| | | |
|---|---|---|
| DE | 3413386 A1 | 10/1985 |
| DE | 20105328 U1 | 7/2001 |
| DE | 102010050919 A1 | 5/2012 |
| DE | 102012003983 A1 | 8/2013 |
| DE | 102012016970 A1 | 3/2014 |
| DE | 102018104942 A1 | 9/2019 |
| DE | 102018130542 A1 | 1/2020 |
| EP | 0513614 A1 | 11/1992 |
| EP | 3434611 A2 | 1/2019 |
| EP | 3434611 A3 | 1/2019 |
| KR | 20010044334 A | 6/2001 |
| WO | 2004089774 A1 | 10/2004 |
| WO | 2019197494 A1 | 10/2019 |
| WO | 2020169778 A1 | 8/2020 |

OTHER PUBLICATIONS

Ermis, Perforated sheet screen baskets, Stainless Steel Screen Baskets, www.ermis-medizintechnik.de, 2018, 1 page.
Office Action received in U.S. Appl. No. 17/432,718 dated May 25, 2023, 29 pages.
Search Report received in German Application No. 10 2019 104 599.1 dated Oct. 31, 2019, with translation, 10 pages.
Search Report received in German Application No. 10 2019 129 061.9 dated Jun. 29, 2020, with translation, 10 pages.
Search Report received in International Application No. PCT/EP2020/054562 dated May 29, 2020, with translation, 6 pages.
Search Report received in International Application No. PCT/EP2020/080009 dated Feb. 5, 2021, with translation, 7 pages.
Written Opinion received in International Application No. PCT/EP2020/054562 dated May 29, 2020, with translation, 11 pages.
Written Opinion received in International Application No. PCT/EP2020/080009 dated Feb. 5, 2021, with translation, 17 pages.

* cited by examiner

STERILISATION CONTAINER FOR RECEIVING STERILE MEDICAL GOODS

CROSS-REFERENCES TO RELATED APPLICATIONS

This application is a continuation of U.S. application Ser. No. 17/772,114, filed on Apr. 26, 2022, which is the United States national stage entry of International Application No. PCT/EP2020/080009, filed on Oct. 26, 2020, and claims priority to German Application No. 10 2019 129 061.9, filed on Oct. 28, 2019. The contents of U.S. application Ser. No. 17/772,114, International Application No. PCT/EP2020/080009 and German Application No. 10 2019 129 061.9 are incorporated by reference herein in their entireties.

FIELD

The present invention relates to a sterile container for receiving cleaned/sterilized medical goods or medical goods to be cleaned/sterilized, having a lower part of the sterile container forming a receiving space for the goods, and a sterile-container lid which is arrangeable in a detachable manner on the lower part of the sterile container for closing the receiving space, wherein at least one handle element is arranged on the lower part of the sterile container, said handle element being positionable between a carrying position projecting from the sterile-container lid and a locking position locking the sterile-container lid to the lower part of the sterile container, wherein a receiving region is formed in the sterile-container lid for completely receiving the handle element therein in the locking position. The invention further relates to a method of manufacturing such a sterile container.

BACKGROUND

Sterile containers for receiving goods to be sterilized, such as medical instruments and devices, are known from the prior art. Such sterile containers are also known as sieve trays or sieve baskets and are used in devices for sterilizing medical devices. The sterile containers loaded with cleaned medical devices, such as drills, scalpels, mirrors, catheters or similar devices, are inserted into a sterile barrier system, for example a sterile container, and are transported to sterilization facilities where the medical devices are sterilized while lying in the sieve tray.

Sterile containers in the form of sieve tray containers are known which have a lower part of the sieve tray forming a receiving region for goods to be sterilized and a sterile-container lid for closing the receiving region of the lower part of the sieve tray, e.g. to prevent light or small instruments from being ejected from the receiving region during a cleaning or washing process, in order to prevent instruments from falling out during transport in sterile barrier systems, on transport trolleys, etc., and to ensure a distance between instruments and soft packaging for the sieve tray so that the latter cannot be damaged. The lower part of the sieve tray and the sterile-container lid are grid-like or have a perforated design to ensure the inflow and outflow of a cleaning, disinfection or sterilization medium.

In order to facilitate handling of closed sieve trays, they have carrying handles which are arranged either on the lower part of the sieve tray or on the sieve tray lid connected thereto. In addition, in order to prevent unintentional opening of the sieve tray lid, it is known to arrange a locking device on the lower part of the sieve tray with which the sieve tray lid can be locked to the lower part of the sieve tray. In some known sieve trays, such a locking function is integrated into the carrying handles. Despite the lid, such carrying handles/locking devices have to be easily accessible for a user of the sieve tray. It is particularly important that the sieve tray can be carried safely, especially when loaded with cleaned instruments. Finally, for transport and storage purposes, it is necessary that several sieve tray containers can be stacked safely and stably when closed, i.e. with lids.

DE 10 2010 050 919 A1 shows a sieve tray container for receiving goods to be sterilized, having a receiving container (lower part of the sieve tray) of grid-like perforated material defining a goods receiving area, said receiving container being closed on one side by a plane, openable lid (sieve tray lid) of grid-like perforated material. At least one locking device is provided on the receiving container, which locks the lid to the receiving container in a closed position of the lid, wherein the locking device is pivotable into a position locking the lid via a locking member attached to the lid, utilizing the spring properties of the locking device and of the locking member. The locking device consists of a bracket-shaped handle which can be pivoted over the plane lid and, in the locked position, rests on the top of the lid and therefore protrudes from the lid surface. It is therefore a disadvantage with this sieve tray that stable and positionally secure stacking of several sieve trays is not possible due to the bracket-shaped handle element protruding above the lid surface, as no level footprint is available for an upper sterile container.

U.S. Pat. No. 8,668,111 B2 discloses a sieve tray having a lower part of the sieve tray and a sieve tray lid having a main panel/lid surface bounded by opposite side edges and opposite end edges. The sieve tray lid forms, via ribs projecting upwards from the surface of the main panel, a receiving region for locking handles pivotably arranged on the lower part of the sieve tray, which in one functional position enable the lower part of the sieve tray to be carried by the user and in another functional position enable the lower part of the sieve tray to be locked to the sieve tray lid, wherein the ribs form a snap-on connection with the locking handles. A disadvantage of this sieve tray is that the handles of the container bottom rest on the main plane of the lid, so that stable stacking of multiple sieve trays is realized by an elaborate lid and bottom structure with further support ribs projecting upward from the surface of the lid. In addition, the geometries shown would be difficult to manufacture from stainless steel sheets and would require a great deal of manufacturing effort.

A further sieve tray is known from the prior art in which two sieve tray handles arranged on opposite sides of the lower part of the sieve tray are inserted in a linearly vertically displaceable manner within the receiving space. The sieve tray handles are each positionable between a pulled-out carrying position and a rest position inserted into the receiving space. Separate closing elements are provided for locking the lid to the lower part. A disadvantage of this sieve tray is that the sieve tray handles are difficult to reach.

Sieve trays are known in which a carrying handle is not arranged on the lower part of the sieve tray, but on the sieve tray lid which is locked with it. Carrying handles arranged on the lid prevent secure and stable stacking of closed sieve trays. In order to prevent this, sieve trays are known in which carrying handles arranged on the lid can be lowered into a recess provided in the lid. However, this still has the disadvantage of unsafe transport, since the entire weight of the sieve tray is borne by the lid and unintentional opening may occur despite the locking mechanism.

A known solution to achieve stable stacking suitability for carrying handles or locking elements arranged on the sieve tray lid is the provision of feet on the underside of the sieve tray container which provide spacing. However, such sieve trays with feet are disadvantageously unsuitable for soft packaging, since the latter can be perforated and damaged by the projecting feet.

Furthermore, relevant prior art also results from DE 10 2018 130 542 A1, DE 201 05 328 U1, U.S. Pat. Nos. 5,065,885 A and 6,012,577 A.

SUMMARY

Against this background, the object of the present invention is to reduce the above-mentioned disadvantages of the prior art, in particular to make a sterile container with lid possible in which handle elements, which in particular enable the sterile container, which is in particular filled and thus heavy, to be carried in a manner which is secure against loss and detachment, to be easily reached and operated by a user, wherein the lower part of the sterile container can be carried via the handle elements (and not by the lid), and stable stacking of several closed sterile containers with lids is possible, wherein furthermore a simple and secure locking function of lower part and lid can be effected.

This object is solved according to the present invention by a sterile container with a lower part of the sterile container forming a receiving space, and a sterile-container lid which is detachably arrangeable on the lower part of the sterile container for closing the receiving space, wherein at least one handle element is arranged on the lower part of the sterile container, said handle element being positionable between a carrying position projecting from the sterile-container lid and a locking position locking the sterile-container lid to the lower part of the sterile container, wherein a receiving region, in particular a receiving region at the border, is formed in the sterile-container lid for receiving the handle element therein in the locking position, wherein the receiving region is formed as a trough like handle recess in the form of a depression projecting into the receiving space relative to the lid plane for completely receiving the handle element therein, and whereby at least one web or transition is formed between the sterile-container lid and the receiving region as a trough like handle recess, which is fluid-permeable at least in sections, preferably perforated like a mesh.

It is a particular advantage of the invention that the trough like handle recess/receiving region is lowered relative to the lid plane or main plane of the sterile-container lid. The receiving region or trough like handle recess receives the handle element of the sieve tray in such a way that, in the closed state, it is positioned below the lid surface, in particular completely below the lid surface, and thus does not protrude above the lid plane or lid surface upwards, i.e. in the direction away from the receiving space. When several such closed and locked containers are stacked, the handle element of the lower part of the sterile container of a lower sterile container is therefore located below the contact area of an upper lower part of the sterile container, so that the upper sterile container comes to rest essentially over its entire surface on the lid plane of the sterile-container lid of the lower sterile container. In addition, the invention ensures that the handle element of the lower part of the sterile container is easily accessible in the locking position and can be easily moved to the carrying position. With the handle element in the carrying position, the sterile container closed with the sterile-container lid can also be carried particularly safely, even when loaded with a relatively high weight, since the handle element is arranged on the lower part of the sterile container. The handle element can be advantageously moved from the locking position to the carrying position and vice versa without having to open or respectively being able to open the lid. Overall, the invention combines a plurality of advantages which have a positive effect in a first aspect on storage suitability/stackability, in a second aspect on portability and in a third aspect on the maintenance of sterility conditions.

The object underlying the invention is further solved by a method of manufacturing a sterile container having a lower part of the sterile container forming a receiving space, and a sterile-container lid for closing the receiving space, in particular a sterile container according to the present description, wherein a receiving region is formed in the sterile-container lid for completely receiving the handle element therein in a locking position, comprising the following steps:

providing a sheet metal, in particular made of a stainless steel material, making slots in the sheet metal to provide a region for deformation between the lid plane and the receiving region to form the trough like handle recess, forming the trough like handle recess for the handle element by deforming the region of the sheet metal provided with slots in the direction facing the receiving space of the lower part of the sterile container.

The sterile container preferably has a substantially rectangular cross-section. One respective trough like handle recess is formed on two opposite sides, preferably the short sides, of the container lid. The opposite trough like handle recesses are preferably formed and arranged mirror-symmetrically to each other. The shape/outer shape of the trough like handle recess preferably corresponds to the outer shape of the handle element.

One embodiment is characterized in that the sterile-container lid has a substantially plane lid surface and the depression projects inward into the receiving space relative to the lid surface. Such a plane lid surface is particularly advantageous in terms of ease of manufacture and cleaning and provides a particularly large bearing area for an additional, stacked sterile container. Preferably, the lid surface lies in a plane with a virtual plane formed by the border of the lower part of the sterile container. This allows the largest possible container volume. In a further embodiment, the lid surface/lid plane may lie below the virtual plane spanned by the border of the lower part of the sterile container, i.e. on the side facing the receiving space. In this way, a border surrounding the top of the lid plane (the side of the lid plane facing away from the receiving space) can be formed on the lid, which is otherwise as plane as possible, in order to serve as a positional safeguard and positioning aid for further sterile containers stacked on the lid.

According to a further embodiment, the receiving region is formed by deforming the lid surface inward into the receiving space. Alternatively, the receiving region may be formed by a sheet metal part attached, in particular welded, to the lid surface. In this case, the connection between the lid surface and the welded sheet metal part may be realized by connection pieces, which are welded at their respective ends either to the lid surface or to the sheet metal part. Furthermore, the connection pieces allow recesses in the transition region between the lid surface and the sheet metal part, whereby the receiving region can be particularly well flushed by a cleaning fluid during cleaning by flushing the recesses in the receiving region with cleaning fluid.

According to a further embodiment, the handle element may be U-shaped with two free legs and a handle piece connecting them. The handle element is preferably hinged with the free legs to the sterile container, in particular to an upper border of the sterile container. As a result of the articulation, it can be moved/positioned particularly easily into the locking position and the carrying position. The advantage of being hinged to the upper border of the lower part of the sterile container is that the receiving regions/the trough like handle recess does not have to be particularly deep in order to ensure that the handle element is completely received and easily accessible to a user. In addition, the size/height of the receiving space of the sterile container is restricted as little as possible. In such a U-shaped handle element, the trough like handle recess has a substantially U-shaped peripheral shape. In other words, the bottom of the trough like handle recess has a peripheral shape corresponding to the shape of the handle element, in this case a substantially U-shaped peripheral shape, and is also preferably plane over its entire surface.

Preferably, the two free legs and the handle piece are plane. In the locking position, they are preferably oriented parallel to the lid surface and/or arranged completely on the side of the lid surface facing the receiving space.

A further embodiment of the invention is characterized in that the sterile-container lid is a perforated sterile-container lid made of a stainless steel sheet. Alternatively or additionally, the lower part of the sterile container may basically be a perforated lower part of the sterile container made of a stainless steel sheet. In this manner, the invention provides a sterile container in the form of a sieve tray container. The trough like handle recess may be manufactured in various ways, for example in the form of separate elements adapted to the lid, or directly from the lid sheet by deformation. The depression forming the trough like handle recess can in particular be formed by a sheet metal part attached, in particular welded, to the lid surface. Alternatively, and as already explained, the depression forming the trough like handle recess may be formed by a deformed region of the lid plane. Both variants permit simple manufacture of a lid which is easy to clean.

A trough like handle recess that is particularly easy to clean can be achieved by forming the deformed region via slots or openings formed in the lid plane that are parallel to each other and form a rhombic grid structure after deformation. In this way, a lid is provided whose trough like handle recess can be rinsed particularly well by a cleaning fluid during cleaning, in that the openings at the trough like handle recess or in the area of the trough like handle recess are rinsed by cleaning fluid. In this embodiment, such portions of the lid/of the lid sheet which are deformed in the manufacturing process are configured virtually according to the principle of an 'expanded metal'. This means that through holes are formed on or respectively in the lid sheet, in particular slot-shaped openings which are produced or present, for example, by a stamping process, and which deform into, for example, rhombic openings as a result of stretching during the deformation of the lid material to the trough like handle recess.

A further embodiment of the sterile container is characterized in that a latching structure is formed in the receiving region for latching with the handle element in the locked position. This can be formed by shaping the lid material in the region of the trough like handle recess. A trough like handle recess which is particularly easy to produce by deformation can be achieved by forming the latching structure as a spring element, in particular made of plastic/injection molding, which is fixed to the sterile-container lid, in particular in the trough like handle recess. It is particularly elegant if the latching element has fixing projections which engage in suitably shaped fixation recesses in the lid material and thus preferably latch. The fixation recesses may be formed, for example, by through holes, in particular punched out, in the lid material.

At this point, it should be noted that the aforementioned latching structure may of course also be provided in another way. Thus, as an alternative to the above embodiment, it may also be manufactured/formed from a plastic, for example an elastomer, preferably a silicone material. This can then be mounted on the lid (material) as a separately manufactured component in the region of the trough like handle recess. In addition, the latching structure may be an elastic molded body, in particular if it is provided as a separate plastic element.

In further embodiments of the method according to the invention, it may also be provided that perforations are formed, in particular punched, in the sheet metal material for the sterile-container lid, wherein these perforations are not deformed when portions of the lid material are formed into trough like handle recesses. In a further embodiment of the method, after all perforations have been formed, the sheet metal material can be subjected to a washing process, optionally followed by a straightening process, for example in the form of roll forming. In a further embodiment, the sheet metal material can then be subjected to a grinding and/or deburring process. Optionally, a further washing process may be carried out. Only after these method steps is the material shaped/formed into the trough like handle recess or the trough like handle recesses, in particular by pressing. Optionally, a preferably fully circumferential border may subsequently be formed as a boundary for further containers according to the invention stacked on the sterile-container lid, again preferably by pressing. It is particularly effective and favorable if the forming of the trough like handle recess/trough like handle recesses and optionally of the stacking border are realized in a single stamping tool or method step.

It can also be said that the invention provides a perforated sterile-container lid made of a stainless steel sheet, which receives the handles of the associated sieve tray or of the sterile container on the front side in trough like handle recesses, which are lowered relative to the main surface in such a way that the handles (incl. optional closure elements) remain below the lid surface in the closed state. In this way, a sterile container/sieve tray can be provided by the invention in which, despite the use of a sterile-container lid, the handle elements are easily accessible to a user, the sterile container or sieve tray can be carried by the handle elements (and not by the lid) and several sterile containers/sieve trays can be stacked on top of each other in a particularly stable manner.

BRIEF DESCRIPTION OF THE DRAWING FIGURES

Figure 2:
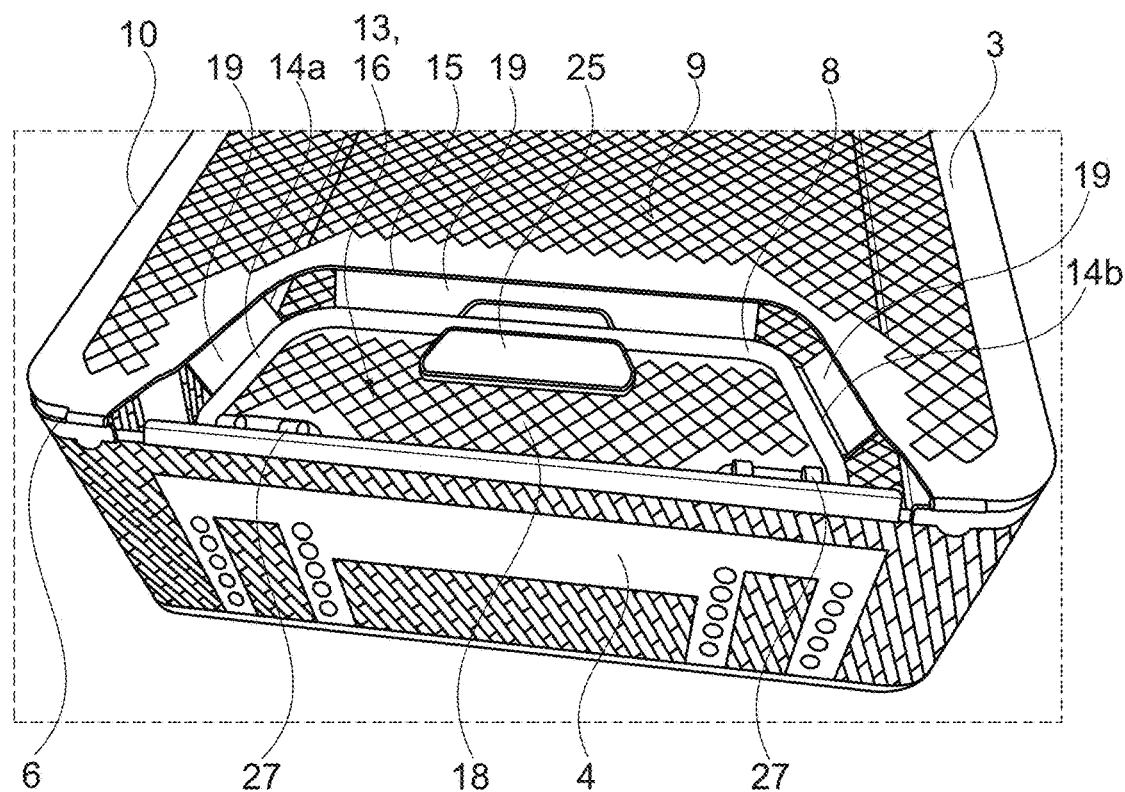
Figure 3:
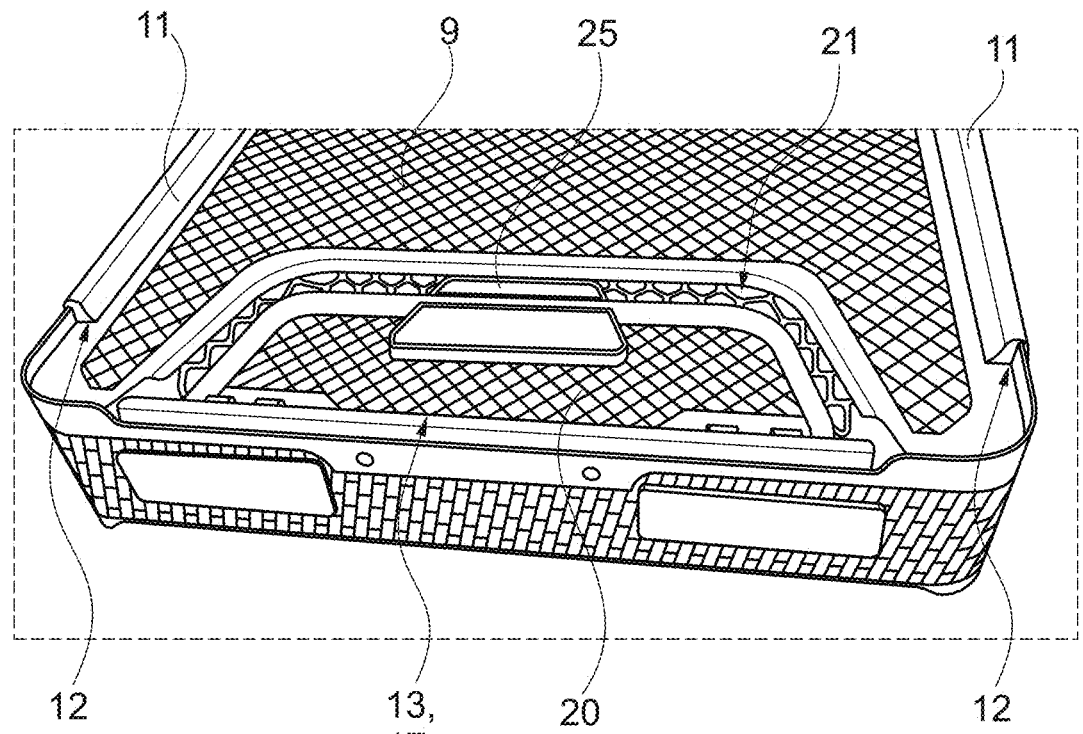
Figure 4:
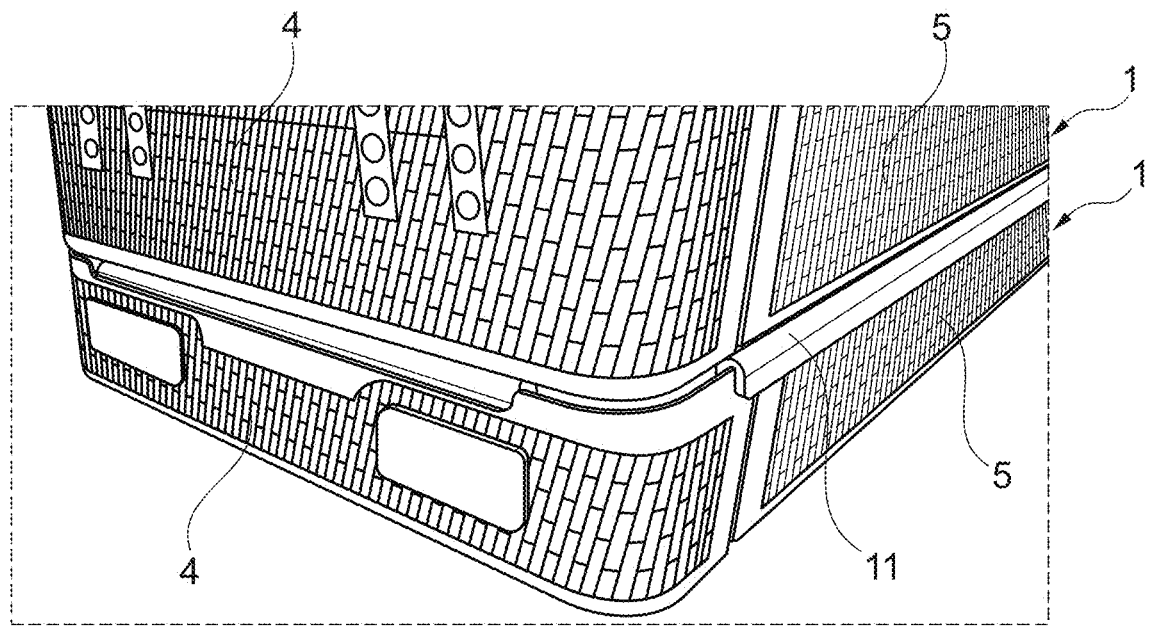
Figure 5:
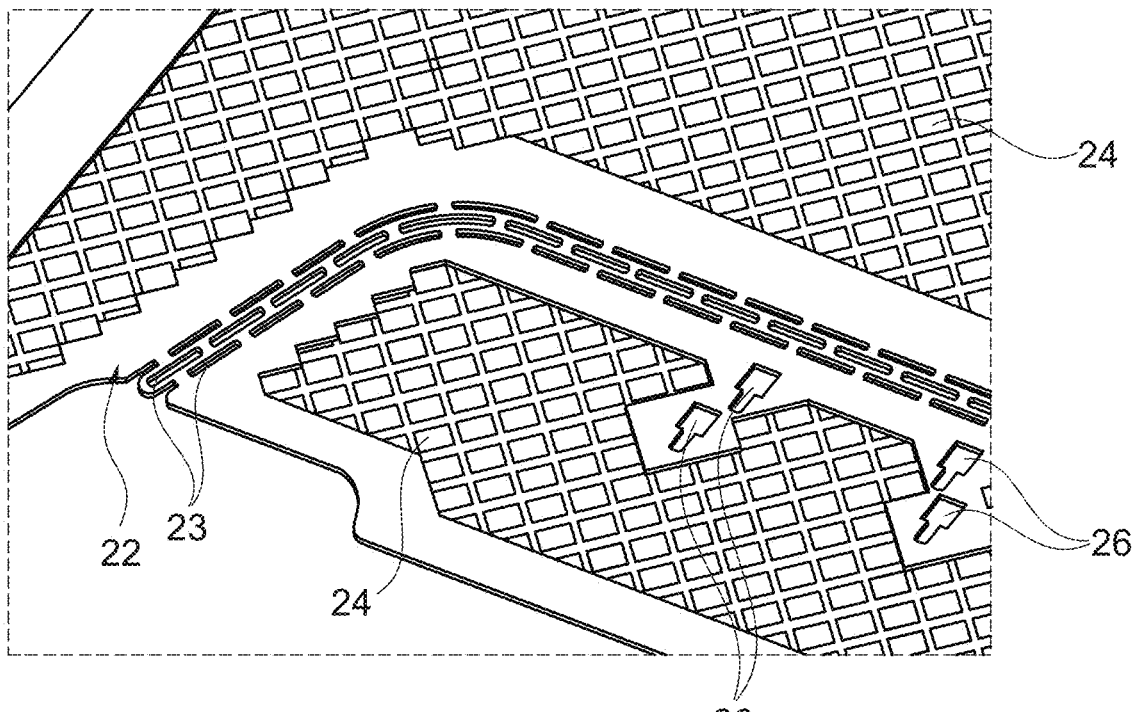
Figure 6:
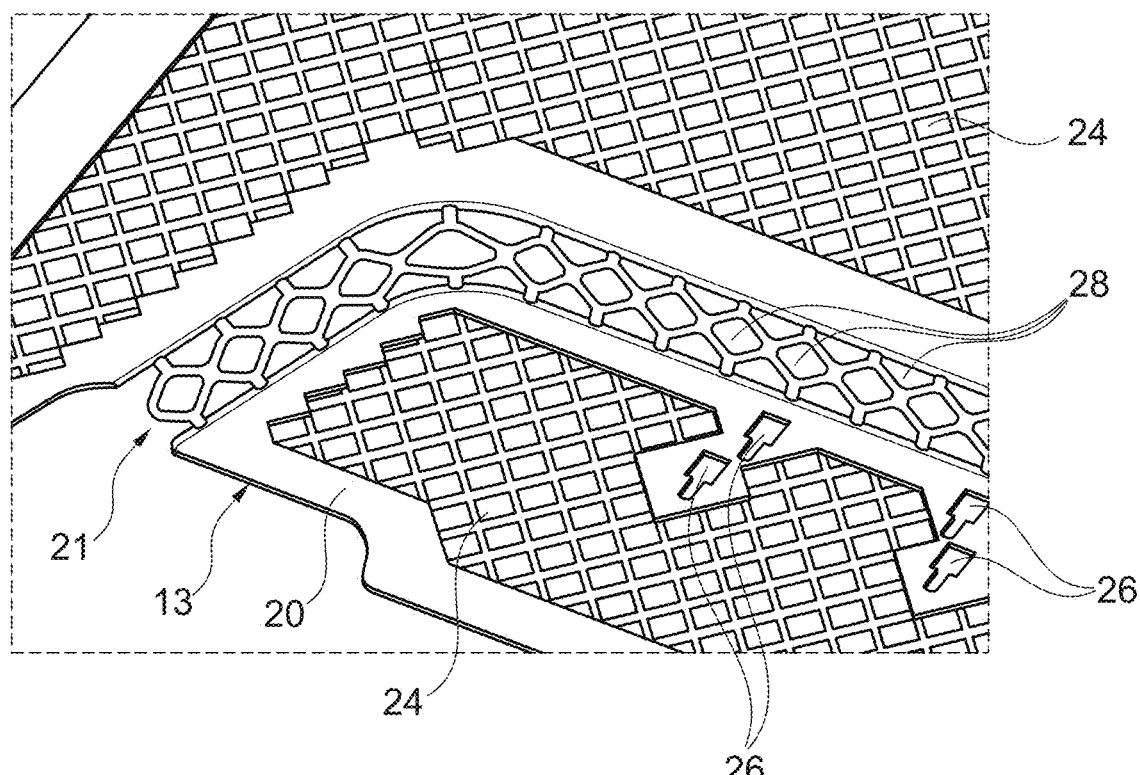

Further features and advantages of the present invention result from the following exemplary and non-limiting description of the figures. These are merely schematic in nature and serve only to aid understanding of the invention. The following is shown:

FIG. 1 shows a perspective view of a sterile container according to a first embodiment of the invention, FIG. 2 shows a perspective view of a portion of a sterile container according to a further embodiment of the invention, FIG. 3 shows a perspective view of a portion of the sterile container of FIG. 1, FIG. 4 shows a perspective view of a part of two stacked sterile containers according to the invention, FIG. 5 shows a perspective view of a part of a die-cutting plate for a sterile-container lid of a sterile container according to the invention, and FIG. 6 shows a perspective view of the part of a die-cutting plate of FIG. 4 with formed trough like handle recesses.

DETAILED DESCRIPTION

FIG. 1 shows a sterile container 1 according to an embodiment of the invention in perspective view. The sterile container 1 is designed as a sieve tray 1, has a lower part 2 of the sterile container and a sterile-container lid 3 and serves to receive sterilized medical goods or goods to be sterilized, which are not shown in the figures. The lower part 2 of the sterile container has a bottom (not shown in the figures), two short side walls 4 arranged thereon and two long side walls 5. The short side walls 4 and the long side walls 5 together form a circumferential lower-part container border 6 and surround a receiving space 7 for the medical goods. Both the lower part 2 of the sterile container and the sterile-container lid 2 are each made of a perforated stainless sheet steel.

The sterile-container lid 3 is detachably arranged on the circumferential border 6 and serves to close the receiving space 7 in such a way that, on the one hand, the goods contained therein are protected from external damage and, on the other hand, the goods contained therein cannot accidentally fall out of the receiving space 7.

A respective handle element 8 is hinged to the lower part 2 of the sterile container on each of the two short side walls 4. This handle element can be positioned between a carrying position projecting from the sterile-container lid 3 (not shown in the figures) and a locking position locking the sterile-container lid 3 to the lower part 2 of the sterile container (shown in the figures). The handle element 8 is essentially U-shaped with two free legs 14a and 14b and a handle piece 15 connecting them. It is hinged with its free legs 14a, 14b in swivel bearing seats 27 on the upper border 6 of the lower part 2 of the sterile container.

The sterile-container lid 3 is designed as a sheet metal die-cut part. It has an essentially plane lid surface 9, which corresponds virtually to the sheet metal surface in the undeformed state. The lid surface 9 forms a contact area or bearing area for stacking a further sterile container 1 (see FIG. 4). In the embodiment shown in FIG. 2, when the container lid 3 is placed on the container border 6, the lid surface 9 is virtually in the plane spanned by the container border 6 or just above it, respectively. In this embodiment, the lid surface 9 is surrounded by a partially circumferential lid border 10. This surrounds the container border 6 and thereby ensures that the container lid 3 has a positionally determined seat on the lower part 2 of the container.

The embodiment shown in FIGS. 1 and 3 differs from the embodiment shown in FIG. 2 in that the lid surface 9 is substantially completely offset from the plane spanned by the container border 6 in the direction of the receiving space 7. This is caused by the fact that the lid plane 9 is surrounded by a lid border 11 projecting upward, i.e. in the direction away from the receiving space 7, whose inner side facing the container border 6 forms a receiving groove 12 for the container border 6.

In the sterile-container lid 3, more precisely in its lid surface 9, a trough like handle recess 13 is formed on both sides. As shown in particular in FIGS. 1, 2 and 3, the handle element 8, which is hinged to the corresponding short side wall 4 and is in the locking position, is completely received in the respective trough like handle recess 13 in such a way that no part of the handle element 8 protrudes outward beyond the lid surface 9.

In all embodiments shown in the figures, the lid surface 9 is substantially plane and the trough like handle recess 13 is in the form of a depression relative to the lid surface 9 projecting into the receiving space 7.

A further difference between the embodiments of FIGS. 1 and 3 on the one hand and FIG. 2 on the other hand is that in the embodiment of FIG. 2, the trough like handle recesses 13 are each formed by a sheet-metal part 16 welded to the lid surface 9, whereas in the embodiment of FIGS. 1 and 3, the trough like handle recesses 13 are each formed by a deformed portion 17. FIG. 2 shows that the sheet metal part 16 has a perforated trough like handle recess bottom 18 and connection pieces 19 arranged thereon, which are welded to the lid surface 9. The deformed portion 17, on the other hand, has a likewise perforated trough like handle recess bottom 20 and a likewise perforated trough like handle recess wall 21 extending between this and the lid surface 9.

In connection with the embodiment of FIGS. 1 and 3, FIGS. 5 and 6 illustrate the manufacture of the trough like handle recess 13 from a plane sheet metal material 22. FIG. 5 shows the sheet metal material 22 in a still undeformed state, while FIG. 6 shows the trough like handle recess 13 formed by deformation. The sheet metal material 22 is provided with first perforations 24, that is in the area of the future lid surface 9 and in the area of the future trough like handle recess bottom 20. Between these two areas, a portion is formed with slot-shaped through holes 23 in the undeformed state (FIG. 5). During deformation from the state shown in FIG. 5 to the state forming the trough like handle recess 13 shown in FIG. 6, the slot-shaped through holes 23 expand to form essentially rhombic perforations 28.

Regardless of the respective embodiment, a latching structure 25 is formed in the trough like handle recess 13 for latching with the handle element 8 in the locked position, more precisely with its handle piece 15. The latching structure 25 is preferably a plastic part 25 that is attached to the sterile-container lid 3 in the trough like handle recess 13. For this purpose, it has fastening elements not shown in the figures, which engage in suitably shaped fixation recesses 26 in the trough like handle recess bottom 18, 20 and thus latch. The fixation recesses 26 are formed here in the form of through holes 26 punched into the lid material.

The invention claimed is:

1. A sterile container for receiving cleaned or sterilized medical goods or medical goods to be cleaned or sterilized, with a lower part of the sterile container forming a receiving space and a sterile-container lid comprising a lid plane and being detachably arrangeable on the lower part of the sterile container for closing the receiving space, at least one handle element being arranged on the lower part of the sterile container, said at least one handle element being positionable between a carrying position projecting from the sterile-container lid and a locking position locking the sterile-container lid to the lower part of the sterile container, a receiving region being formed in the sterile-container lid for receiving the at least one handle element in the receiving region in the locking position,
- the receiving region being formed as a trough like handle recess comprising a depression projecting into the receiving space relative to the lid plane for completely receiving the at least one handle element in the receiving region,
- the trough like handle recess comprising at least one sheet metal part fixed to the lid plane, and
- the at least one handle element being U-shaped with two free legs and a handle piece connecting the two free legs to each other and is hinged with the two free legs to the lower part of the sterile container.

2. The sterile container according to claim 1, wherein the trough like handle recess is formed by the at least one sheet metal part welded to the lid plane.

3. The sterile container according to claim 1, wherein the at least one sheet metal part has a perforated trough like handle recess bottom and connection pieces, the connection pieces being arranged on the perforated trough like handle recess bottom and welded to the lid plane.

4. The sterile container according to claim 1, wherein the lid plane lies in or above a virtual plane spanned by a container border of the lower part of the sterile container.

5. The sterile container according to claim 4, wherein the at least one handle element is hinged in a swivel bearing seat on the container border of the lower part of the sterile container.

6. The sterile container according to claim 1, wherein the two free legs and the handle piece are planar and, in the locking position, are oriented parallel to the lid plane and/or, in the locking position, are arranged completely on a side of the lid plane facing the receiving space.

7. The sterile container according to claim 1, wherein at least a portion of the sterile-container lid is flat and conforms to the lid plane, and the depression projects inwardly into the receiving space relative to the lid plane.

8. The sterile container according to claim 1, wherein the sterile-container lid is perforated and made of a stainless steel sheet.

9. The sterile container according to claim 1, further comprising a latching structure formed in the trough like handle recess for latching with the at least one handle element in a locked position.

10. The sterile container according to claim 9, wherein the latching structure is formed by a spring element fixed to the sterile-container lid.

11. A method of manufacturing the sterile container according to claim 1 comprising the following steps:
- providing the at least one sheet metal part;
- forming the trough like handle recess by attaching the at least one sheet metal part to the lid plane so that the receiving region is deformed in a direction facing the receiving space of the lower part of the sterile container.

12. The method of manufacturing the sterile container according to claim 11, wherein the receiving region is formed by the at least one sheet metal part welded to the lid plane.

13. The method of manufacturing the sterile container according to claim 11, wherein a connection between the lid plane and the at least one sheet metal part is realized by connection pieces having ends that are welded either to the lid plane or to the at least one sheet metal part.

* * * * *